United States Patent [19]

Adkisson

[11] Patent Number: 5,266,028
[45] Date of Patent: Nov. 30, 1993

[54] TRANSLINGUAL ORTHODONTIC DEVICE AND METHOD OF USE FOR SAME

[76] Inventor: Gregory H. Adkisson, 4170 Jackdaw, San Diego, Calif. 92103

[21] Appl. No.: 959,365

[22] Filed: Oct. 13, 1992

[51] Int. Cl.⁵ ............................................. A61C 3/00
[52] U.S. Cl. ........................................ 433/18; 433/24
[58] Field of Search ............................ 433/18, 19, 24

[56] References Cited

U.S. PATENT DOCUMENTS

| | | | |
|---|---|---|---|
| 3,618,214 | 11/1971 | Armstrong | 433/19 |
| 3,690,003 | 9/1972 | Gerber | 433/19 X |
| 4,708,646 | 11/1987 | Jasper | 433/19 |
| 4,815,972 | 3/1989 | Howe | 433/18 X |
| 5,066,226 | 11/1991 | Summer | 433/19 |

*Primary Examiner*—Gene Mancene
*Assistant Examiner*—Nicholas D. Lucchesi
*Attorney, Agent, or Firm*—Brown, Martin, Haller & McClain

[57] ABSTRACT

A method and apparatus for use with translingual elastic bands in orthodontic procedures is disclosed. According to the method, a translingual band is attached to a hook and wire which are extended through a semi-rigid sheath. The sheath is presized to fit snugly between the inner surfaces of opposing teeth in a patient's mouth.

The band is attached appropriately to a tooth then pulled by the hook and wire through the sheath and attached to an opposing tooth. The sheath is rotatable about the band and is left in place to protect the patient's tongue and soft palette. The sheath will be measured and downsized as treatment progresses.

7 Claims, 1 Drawing Sheet

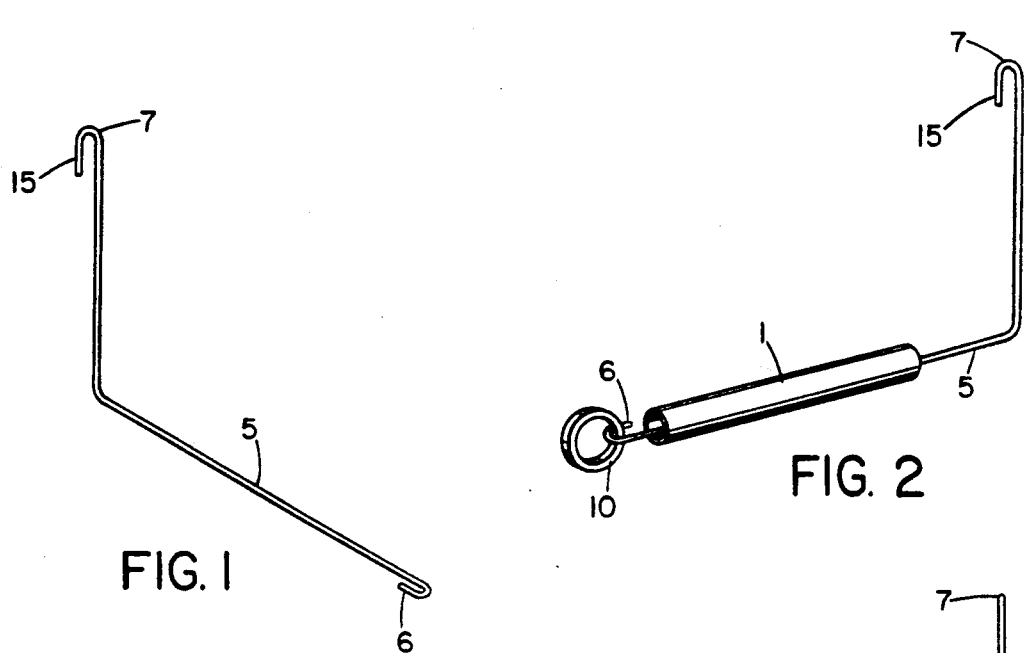
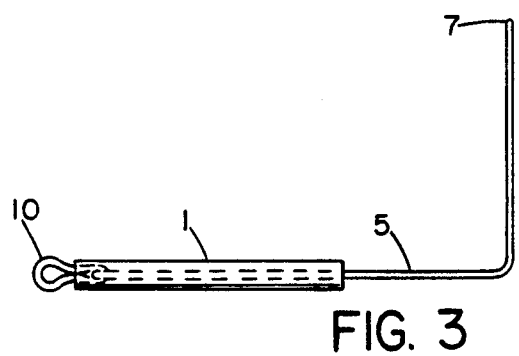
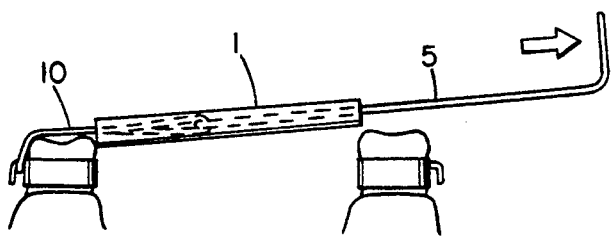
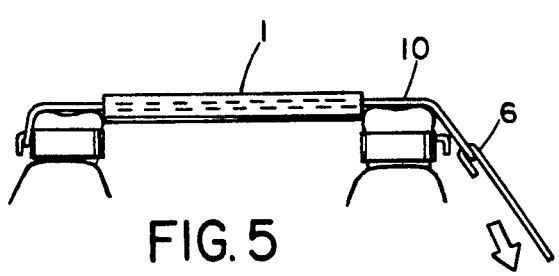
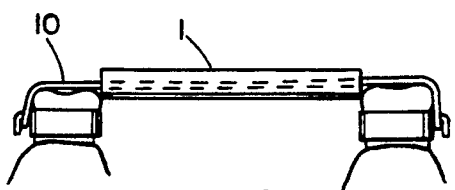
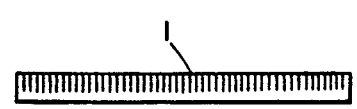

TRANSLINGUAL ORTHODONTIC DEVICE AND METHOD OF USE FOR SAME

FIELD OF THE INVENTION

This invention relates to an orthodontic device, more particularly one for use with translingual elastics used to move teeth inwardly in a patient's mouth.

BACKGROUND OF THE INVENTION

Translingual application of elastic bands is considered the most effective orthodontic means of moving teeth inwardly towards the midline of the patient's mouth. Translingual refers to the fact that the elastic band is applied from one molar tooth, across the tongue to the molar tooth on the opposite side to move the teeth inwardly. Its major drawback is lack of patient compliance due to extreme discomfort. The discomfort comes from the fact that the tongue is constantly abraded by the taut elastic band running side to side. The actions of speaking, talking, swallowing or simply moving the tongue cause enough discomfort that the patient quickly becomes discouraged and removes the elastic. Both the upper and lower surfaces of the tongue are affected and the discomfort is particularly intense on the softer lower area of the tongue and soft palette. The orthodontist is then forced to revert to alternative means of moving the teeth.

These alternative methods of moving teeth are less than desirable for two reasons. First, they are less effective than translingual bands in most cases and result in a longer treatment. Second, they also have the tendency to cause undesired movement of teeth other than those targeted and the orthodontist must often go back and correct these secondary changes. As a result, treatment is prolonged.

A typical alternative method of moving teeth is accomplished by extending the elastic bands from the outside lower molar to the inside upper molar. This method moves the lower teeth inward but may also cause motion in several undesired directions by both the upper and lower teeth. This undesired motion is called "vertical extrusion" and is one of the secondary changes that must be corrected.

The discomfort caused by the conventional attachment and use of translingual elastic bands is avoided by the present invention, which allows treatment to proceed in a time-effective and accurate manner.

SUMMARY OF THE INVENTION

The inventive device consists of a set of translingual bands, a wire and hook for attaching the bands to the appropriate molars and a customized sheath which rotatably surrounds the bands and extends entirely from the inner surface of one molar to the other. The sheath is preferably formed of a biologically inert, semirigid plastic and is tubular in shape with a smooth outer surface.

In use, the patient's orthodontist sizes the tubing then threads the elastic therethrough using the wire and hook. Once the hook and band are situated correctly within the sheath, the band is attached to the first molar then pulled through the sheath for attachment to the second molar. The hook is then removed, leaving the sheath in place.

In a preferred embodiment, the sheath will have graduated markings thereon to allow for simple visual measurement of the movement of the teeth and subsequent resizing of the sheath.

BRIEF DESCRIPTION OF THE DRAWINGS

FIG. 1 is a perspective view of the applicator wire;

FIG. 2 is a perspective view with a protective sheath and a rubber band on the wire;

FIG. 3 is a side elevational view of the applicator wire with the rubber band pulled slightly into the sheath ready for application;

FIG. 4 illustrates the initial step of applying the rubber band between a pair of molars;

FIG. 5 illustrates the rubber band pulled completely through the sheath;

FIG. 6 illustrates the rubber band secured to the molars with the sheath between; and FIG. 7 is a side elevational view of a protective sheath with incremental marketings for length reference.

DETAILED DESCRIPTION OF THE PREFERRED EMBODIMENTS

A. Apparatus

FIG. 1 depicts the wire 5 of the invention while FIG. 2 shows wire 5 in use with sheath 1. Sheath 1 is tubular in shape and will have an inner diameter sized to just allow clearance and rotation therein of wire 5 and an elastic band (for example, as shown in FIG. 3). It is expected that for use with most bands, an inner diameter of $\frac{1}{8}-\frac{1}{4}$ of an inch will be sufficient.

The total width of the sheath will vary with the inner diameter, but will be approximately 1/4 of an inch for most applications. The purpose of the sheath is to provide a smooth, curved covering for the bands which will not abrade the soft tissue of the tongue and palette and which provides greater comfort relative to a bare band. To this same end, the sheath must also rotate easily about the band. The total width of the sheath will, therefore, be dictated by these two considerations.

The sheath may be made of any biologically inert material, but will preferably be of a semirigid plastic which will not significantly soften at temperatures below 120° C. (thereby maintaining structural integrity within the patient's mouth). The material chosen should also be capable of warming while in the patient's mouth so it does not feel noticeably cool. Flexible polyvinyl chloride plastics, such as those used in medical tubing and catheters, are suitable. Sources for this material may be found by reference to Rubin, "Handbook of Plastic Materials and Technology" (1990) ch. 43.14.

Wire 5 will be of a horizontal length longer than the length of sheath 1. The length of sheath 1 will be modified by the orthodontist as described further below. Wire 5 may be formed of any autoclavable material but will preferably be formed of bendable stainless steel wire. As shown in FIG. 1, wire 5 is formed of 1/32 to 1/16 diameter wire. As shown in FIG. 1, wire 5 is an elongated straight wire with a small bend in the shape of a hook 6 at one end. The end 7 opposite hook 6 may be bent perpendicularly away from the length of the wire so it is more easily gripped while in use and may have a second hook 15 thereon.

The translingual bands to be used with the inventive device are conventional and are available through usual orthodontic supply sources.

B. Method

The orthodontist first sizes sheath 1 to fit snugly between the patient's lower molars. Sizing is accomplished by precisely measuring the distance between the molars and cutting the sheath accordingly. To insure that the cut end is substantially free of rough edges, the sheath should be cut with a sharp edge, such as a razor blade. When in place, there should be no noticeable gap between the patient's molars and the ends of sheath 1. The snugger the fit, the more that chafing of the patient's tongue will be avoided. A properly placed sheath is depicted in FIG. 6.

Once sheath 1 is properly sized, wire 5 is inserted therethrough so hook 6 extends beyond end 8 of sheath 1. An appropriate translingual band 10 is then attached to hook 6, the inner diameter of which is sized so band 10 is snugly seated therein. It is expected that to this end an inner diameter in hook 6 of approximately 1/32 to 1/16th of an inch will suffice for most bands. Preferably, wire 5 will be drawn back into sheath 1 so hook 6 is wholly or partially surrounded thereby, leaving band 10 extending out of sheath 1 (as shown in FIG. 3). This will maintain band 10 in a loop shape so it can be more easily attached to a molar and will help to secure the band onto hook 6 while it is being attached to a tooth.

Band 10 is then placed around the first molar as shown in FIG. 4 to form a buccal attachment (dental attachment on the cheek side of the molar) as will be familiar to those skilled in orthodontics. Once band 10 is so attached, it is pulled through and out of sheath 1 by wire 5, as shown in FIG. 5, to form an opposite, second buccal attachment. Wire 5 is then removed at hook 6 from band 10 (or hook 6 may be removed just prior to the second buccal attachment). Once attachment is complete, all of the surface areas of band 10 (except those surrounding the opposing molars) will be covered by sheath 1, thus protecting the patient's tongue and soft palette from abrasion and chafing by the band during treatment.

In an alternate and preferred embodiment, sheath 1 will have graduated markings at millimeter intervals on its outer surface (see FIG. 7). As treatment progresses and the patient's teeth are moved inwardly, that movement may be visually measured and sheath 1 resized along its markings as shown in FIG. 7. This resizing may be done by the orthodontist or by the patient, who would in that case be instructed to return to the orthodontist after a predetermined movement (such as 2 to 3 millimeters) has occurred. This self-evaluation will not only reduce the overall cost of treatment by limiting the number of orthodontic appointments necessary, it may also avoid overcorrection by alerting the patient to any excessive movement which may occur in between scheduled appointments.

Although preferred embodiments of the inventive apparatus and method for use thereof are disclosed, it will be appreciated by those skilled in the art that modification may be made without departing from the scope or spirit of the invention, which is defined by the claims appended hereto.

I claim:

1. An orthodontic treatment apparatus, comprising:
a semirigid sheath having opposite first and second ends, the sheath being of predetermined length for fitting snugly between the inner surfaces of opposing teeth in a patient's mouth;
an elongated wire of length greater than the length of the sheath, the wire having two opposing ends, one of said ends being bent in the shape of a hook, the wire comprising means for extending through said sheath with the hook extending beyond the first end of the sheath and the opposite end of the wire extending through the second end of the sheath in a first operative position of the apparatus;
a translingual elastic band comprising means for attaching to said hook and to a first tooth on one side of a patient's mouth in said first operative position;
said wire further comprising means for pulling said hook and attached band through said sheath for attaching said band to a second tooth on the opposite side of the patient's mouth in a second operative position of said apparatus; and
said sheath having an inner diameter sufficient to allow rotation thereof about said wire in said first operative position and about said band in said second operative position.

2. An orthodontic treatment apparatus, comprising:
an elongated wire having two opposing ends, one of said ends being bent in the shape of a hook;
a translingual band for attachment to said hook; and
a semirigid sheath having an inner diameter sufficient to allow rotation thereof about said wire and said band, said semirigid sheath having a series of graduated markings on the outer surface thereof, said markings comprising sizing means for allowing said sheath to be adjusted to fit snugly between the inner surfaces of opposing teeth in a patient's mouth.

3. An apparatus according to claim 2 wherein said semirigid sheath is formed of flexible polyvinyl chloride plastic.

4. A method for use of translingual orthodontic elastic bands comprising:
extending an elongated wire having two opposing ends, one of said ends being bent to form a hook, through a semirigid sheath which has first and second ends and has ben pre-sized to fit snugly between the inner surfaces of teeth in a patient's mouth, said extension made so said hook extends beyond the first end of the sheath and the opposite end of the wire extends beyond the second end of the sheath,
attaching a translingual elastic band to said hook,
forming a first buccal attachment of said band on a first side of the patient's mouth,
pulling said hook and band through the sheath and beyond the second end of said sheath, wherein said sheath is then rotatable about said band, and
forming a second buccal attachment of said band on a second side of the patient's mouth opposing the first side of the patient's mouth.

5. A method according to claim 4 wherein said semirigid sheath is sized downwardly as treatment progresses.

6. A method according to claim 5 wherein said downward sizing is measured by graduated markings on the outer surface of said semirigid sheath.

7. A method according to claim 4 further comprising the step of pulling said hook and band back into said sheath just far enough to form a loop in said band prior to forming the first buccal attachment.

* * * * *